(12) United States Patent (10) Patent No.: US 12,691,140 B2
Traverso et al. (45) Date of Patent: Jul. 28, 2026

(54) THERAPEUTIC CARBON MONOXIDE FORMULATIONS

(71) Applicants: THE BRIGHAM AND WOMEN'S HOSPITAL, INC., Boston, MA (US); MASSACHUSETTS INSTITUTE OF TECHNOLOGY, Cambridge, MA (US); BETH ISRAEL DEACONESS MEDICAL CENTER, INC., Boston, MA (US)

(72) Inventors: Carlo Giovanni Traverso, Boston, MA (US); James D. Byrne, Boston, MA (US); Hannah Boyce, Boston, MA (US); Leo E. Otterbein, Boston, MA (US); David J. Gallo, Boston, MA (US)

(73) Assignees: THE BRIGHAM AND WOMEN'S HOSPITAL, INC., Boston, MA (US); MASSACHUSETTS INSTITUTE OF TECHNOLOGY, Cambridge, MA (US); THE BETH ISRAEL DEACONESS MEDICAL CENTER, INC., Boston, MA (US)

( * ) Notice: Subject to any disclaimer, the term of this patent is extended or adjusted under 35 U.S.C. 154(b) by 467 days.

(21) Appl. No.: 18/024,347

(22) PCT Filed: Sep. 8, 2021

(86) PCT No.: PCT/US2021/049457
§ 371 (c)(1),
(2) Date: Mar. 2, 2023

(87) PCT Pub. No.: WO2022/055991
PCT Pub. Date: Mar. 17, 2022

(65) Prior Publication Data
US 2023/0398141 A1 Dec. 14, 2023

Related U.S. Application Data

(60) Provisional application No. 63/075,331, filed on Sep. 8, 2020.

(51) Int. Cl.
*A61K 33/00* (2006.01)
*A61K 9/12* (2006.01)
(Continued)

(52) U.S. Cl.
CPC .............. *A61K 33/00* (2013.01); *A61K 9/122* (2013.01); *A61K 45/06* (2013.01); *A61K 47/36* (2013.01); *A61P 1/04* (2018.01)

(58) Field of Classification Search
CPC ........ A61K 33/00; A61K 9/122; A61K 45/06; A61K 47/36; A61K 1/04; A61K 9/0053;
(Continued)

(56) References Cited

U.S. PATENT DOCUMENTS 3,086,370 A * 4/1963 Barnes .................... C01B 32/55
62/46.1
4,263,328 A * 4/1981 Parada .................... A23G 3/42
426/453
(Continued)

FOREIGN PATENT DOCUMENTS

EP 2124631 B1 * 8/2012 ............... A23G 3/54
EP 1771503 B1 * 9/2014 ............... F26B 5/06
(Continued)

OTHER PUBLICATIONS

Department of Atmospheric and Climate Science [online] retrieved on 7/22/5 from: https://www.atmos.washington.edu/~dennis/321/ Chapter_01_Tables.pdf; 3 pages). (Year: 2025).*
(Continued)

*Primary Examiner* — Ernst V Arnold
(74) *Attorney, Agent, or Firm* — Tarolli, Sundheim, Covell & Tummino LLP

(57) ABSTRACT

A pharmaceutical composition is described that includes a pharmaceutical carrier comprising gas pockets containing carbon monoxide gas, wherein the pharmaceutical carrier is a foam, a solid, or a hydrogel. Methods of using the pharmaceutical composition to treat an inflammatory dis-
(Continued)

B  FOAM GEM  SOLID GEM  HYDROGEL GEM ease or condition, and methods of making the pharmaceutical composition, are also described.

25 Claims, 6 Drawing Sheets

(51) Int. Cl.
*A61K 45/06* (2006.01)
*A61K 47/36* (2006.01)
*A61P 1/04* (2006.01)

(58) Field of Classification Search
CPC ........ A61K 47/02; A61K 47/12; A61K 47/26; A61K 47/38; A61K 9/0031
See application file for complete search history.

(56) References Cited

U.S. PATENT DOCUMENTS

| | | | | |
|---|---|---|---|---|
| 4,289,794 | A * | 9/1981 | Kleiner | A23G 3/0221 426/660 |
| 4,347,707 | A * | 9/1982 | Zemelman | A23B 2/85 62/69 |
| 7,691,416 | B2 | 4/2010 | Otterbein et al. | |
| 8,722,749 | B2 | 5/2014 | Durance et al. | |
| 2004/0067261 | A1 | 4/2004 | Haas et al. | |
| 2006/0204557 | A1 * | 9/2006 | Gupta | A61K 33/14 424/443 |
| 2010/0158813 | A1 | 6/2010 | Paradossi et al. | |
| 2011/0038955 | A1 | 2/2011 | Rodrigues et al. | |
| 2013/0289471 | A1 | 10/2013 | Ward et al. | |
| 2013/0309279 | A1 * | 11/2013 | Gomperts | A61P 9/02 424/699 |
| 2017/0072023 | A1 | 3/2017 | Abuchowski et al. | |

FOREIGN PATENT DOCUMENTS

| | | | | |
|---|---|---|---|---|
| WO | WO-2009102487 A2 * | 8/2009 | ............ | A61L 15/44 |
| WO | 2019235165 A2 | 12/2019 | | |

OTHER PUBLICATIONS

Carter, SW (How to Use Xanthan Gum [online] retrieved on Jul. 22, 25 from: https://renecarter.wordpress.com/2015/01/11/how-to-use-xanthan-gum/; Jan. 11, 2015; 5 pages). (Year: 2015).*
Extended European Search Report for corresponding Application No. /Patent No. 21867509.8-1109 / 4210732 PCT/US2021049457, Applicant The Brigham & Women's Hospital, Inc., et al., with a mailing date of Sep. 20, 2024, 9 pages.
Otterbein et al., Nat Med 6, 422-428 (2000).
R. Motterlini, L. E. Otterbein, Nat Rev Drug Discov 9, 728-743 (2010).
Fredenburgh et al., JCI Insight 3, (2018).
Rosas et al., Chest 153, 94-104 (2018).
Hopper et al., Curr Pharm Des 24, 2264-2282 (2018).
Takagi et al., Free Radical Research, vol. 50, No. 10, pp. 1098-1105, 2016.
Nakao et al., Am J Transplant, vol. 6, No. 10, pp. 2243-2255, 2006.
Belcher et al., Plos One, vol. 13, No. 10, p. e0205194, 2018.
Ji et al., J Pharm Sci 105, 406-416 (2016).
Magierowska et al., Int J Mol Sci 17, 442 (2016).
Nakao et al., J Pharmacol Exp Ther 319, 1265-1275 (2006).
Zheng et al., Nat Chem 10, 787-794 (2018).
Watson et al., J Anal Toxicol 11, 19-23 (1987).
Yan et al., Redox Biol 17, 274-283 (2018).
Tenhunen et al., Proc Natl Acad Sci U S A 61, 748-755 (1968).
Coburn, Ann N Y Acad Sci 150, 13-21 (1968).
Steiger et al., J Control Release 239, 128-136 (2016).
Correa-Costa et al., Proc Natl Acad Sci U S A 115, E2302-E2310 (2018).
Gutierrez et al., J Appl Physiol (1985) 58, 558-563 (1985).

\* cited by examiner

A

B

C

D

A

B

C

D

E

F

A

B

THERAPEUTIC CARBON MONOXIDE FORMULATIONS

CROSS-REFERENCE TO RELATED APPLICATIONS

This application claims the benefit of U.S. Provisional Application No. 63/075,331, filed Sep. 8, 2020. This provisional application is hereby incorporated by reference in its entirety.

TECHNICAL FIELD

The present disclosure relates generally to pharmaceutical gas entrapping compositions including carbon monoxide gas, and their use for treating inflammatory diseases or conditions.

BACKGROUND

Carbon monoxide (CO), an odor and colorless gas, has long been recognized as a silent killer owing to its strong affinity to hemoglobin. Carbon monoxide competitively displaces oxygen to form carboxyhemoglobin (COHb), thereby decreasing the body's oxygen-carrying capacity. Generally, if COHb accounts for more than 50%, it may result in coma, convulsions, depressed respiration and cardiovascular status or even fatal consequences. Conversely, at lower concentrations, CO acts as a gasotransmitter with beneficial properties akin to nitric oxide and hydrogen sulfide, and has been implicated in a range of diverse physiological and pathological processes. Carbon monoxide has well-established anti-inflammatory effects exerted through the Heme Oxygenase-1 (Hmox1, HO-1) pathway, which is implicated in adaptive cellular responses to stressful stimuli and injury. Otterbein et al., Nat Med 6, 422-428 (2000). Carbon monoxide has been shown to be beneficial for the treatment of many diseases in numerous preclinical models, including cardiovascular disorders, sepsis and shock, acute lung, kidney and liver injury, infection, and cancer. R. Motterlini, L. E. Otterbein, Nat Rev Drug Discov 9, 728-743 (2010).

Given the demonstrated benefits, therapeutic CO delivery by inhalational has been evaluated in numerous clinical trials. Fredenburgh et al., JCI Insight 3, (2018); Rosas et al., Chest 153, 94-104 (2018). The most common method of carbon monoxide administration is through low levels of inhaled gas, 100-250 ppm CO mixed with air, which has been shown to treat colitis, reperfusion ischemia, and sickle cell disease. Hopper et al., Curr Pharm Des 24, 2264-2282 (2018). Inhalational delivery, however, presents significant challenges given the variability in patient ventilation, environmental safety concerns for patients and healthcare workers, and the need for large amounts of compressed CO gas in cylinders.

Other methods of administration that have more recently been developed include carbon monoxide saturated solutions, such as saline (Takagi et al., Free Radical Research, vol. 50, no. 10, pp. 1098-1105, 2016), ringer's lactate solution (Nakao et al., Am J Transplant, vol. 6, no. 10, pp. 2243-2255, 2006), and a lipid rich solution (Belcher et al., PLoS ONE, vol. 13, no. 10, p. e0205194, 2018). However, these solutions are only able to encapsulate a small amount of carbon monoxide, at a concentration of about 500 μM CO, or 1.4% mass of CO in solution. Other advancements have shown an increase in carboxy bound hemoglobin (% CO-Hb) from 1.6% to 5.4% in NY1DD mice when given a dose of 10 mL/kg of a lipid rich CO solution (Belcher et al., Ibid.). CO-releasing molecules (CORMs) and COHb infusions have also been developed. X. Ji et al., J Pharm Sci 105, 406-416 (2016); Magierowska et al., Int J Mol Sci 17, 442 (2016).

These alternatives face significant limitations either due to toxicity of transition metals present in the formulations or lack of potency. An oral liquid with dissolved CO is also being developed to deliver CO primarily through the stomach, but the tunability of the formulation is unclear. Belcher et al., Ibid). Accordingly, there remains a need for improved methods of therapeutic CO delivery.

SUMMARY

To address administration obstacles present for existing methods of administering carbon monoxide, gas entrapping materials (GEMs) capable of delivering carbon monoxide were developed having an increased ratio of encapsulated gas in liquid and solid matrices that would be easy to administer orally or rectally. In order to create ingestible carbon monoxide encapsulated products, the main criteria were: 1) encapsulate as much CO gas as possible to limit the volume of dosage required; 2) ensure product is stable at room temperature in atmospheric pressure to allow for safe administration; 3) when administered into the body the CO will release safely and steadily; 4) the potential devices used to administer the CO systems would allow for safe pressurization with carbon monoxide; 5) the CO dosage will be easy to determine based on the amount of product that will be administered; 6) the dosage of the product can easily be measured and controlled; 7) different doses of CO can be achieved by changing the amount of encapsulated CO through dosage change or CO pressure change; 8) develop a product that could have a shelf life up to one week to one month; and 9) the product could be safely stored in a patient's home with minimal extra safety precautions.

The pharmaceutical compositions described have a higher carbon monoxide concentration and higher stability than previously developed carbon monoxide containing solutions. This was accomplished using both liquid and solid formulations, including a multicomponent formulation contained a foaming agent(s) and thickening agent(s) to create a foam product, and a multicomponent foam-gel system that also used foaming agent(s) and thickening agents(s) dispensed into a crosslinked solution, a solidified sugar matrix to trap the gas, and other solid or liquid products that are generally recognized as safe (GRAS) and able to trap air bubbles in a liquid or solid matrix.

The foam composition can trap more carbon monoxide given its colloidal characteristics that entrap higher amounts of gas compared to aerated beverages. Additionally, a solid sugar matrix is able to trap high pressure carbon monoxide and therefore deliver a higher dose of carbon monoxide in a smaller volume and it stable at room temperature and atmospheric pressure when stored with a desiccant. These developments allow for a smaller and more effective dosing compared to previously developed liquid carbon monoxide formulation. These systems are also easy to administer at home with a stable, ingestible system of carbon monoxide products.

BRIEF DESCRIPTION OF THE FIGURES

The foregoing and other features of the present disclosure will become apparent to those skilled in the art to which the present disclosure relates upon reading the following description with reference to the accompanying drawings.

DETAILED DESCRIPTION

Figures 1A, 1B, 1C, 1D:
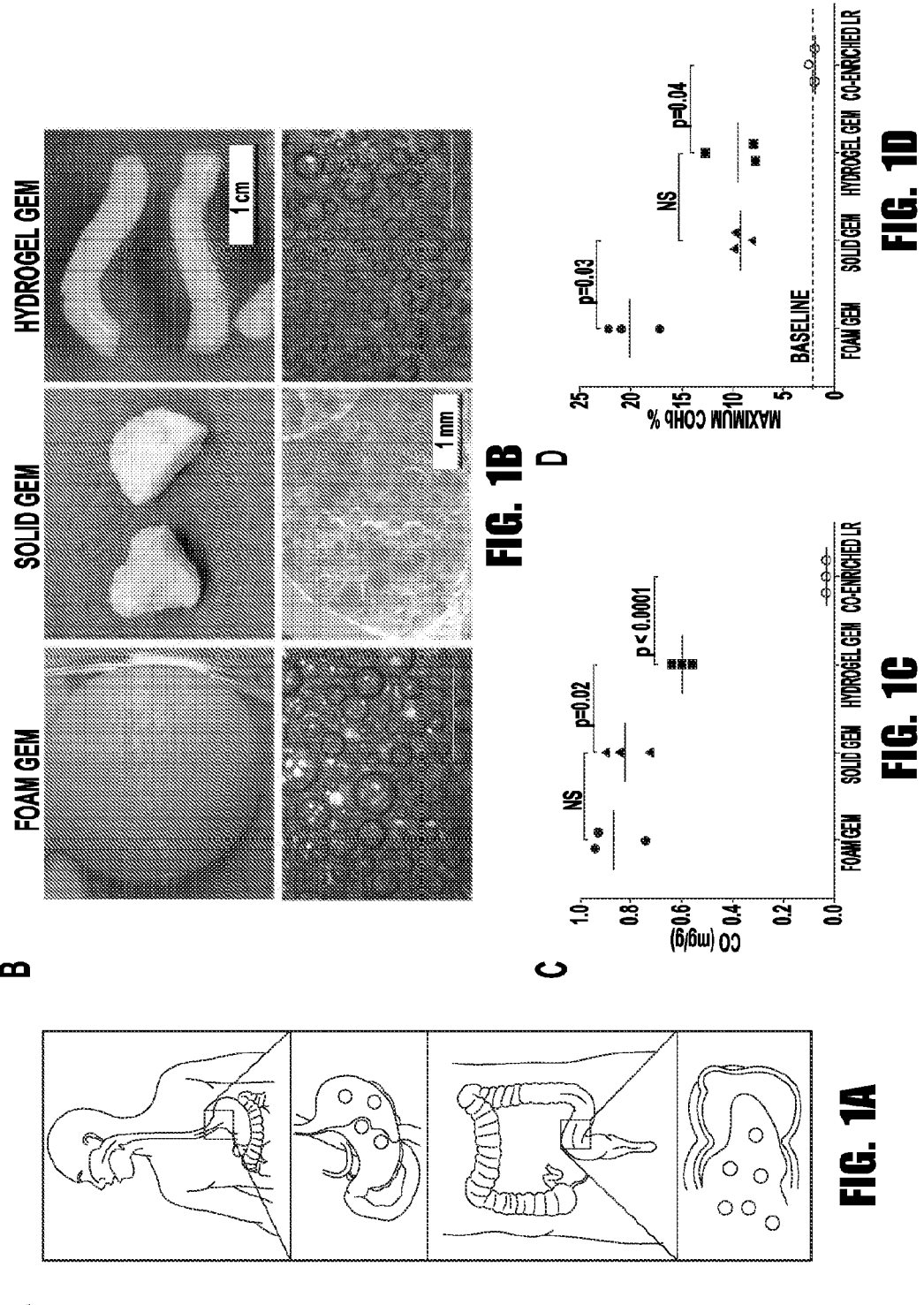
FIGS. 1A-1D provide graphs and images showing materials for delivery of CO. (A) GEMs may be administered orally or rectally. (B) Macroscopic and microscopic images of three GEMs, including foam GEMs, solid GEMS, and hydrogel GEMs. (C) Quantity of CO in each formulation compared to CO-enriched Lactated Ringer's solution (LR). (D) Maximum carboxyhemoglobin (COHb) achieved for each GEM administered through the GI tract. The foam GEMs were rectally administered (5 g/kg), and the solid GEMs (5 g/kg) and hydrogel GEMs (5 g/kg) were surgically placed in the stomach. The CO-enriched LR was administered via oral gavage (5 g/kg). Data are means (n=3). P values were determined by unpaired t test. NS, not significant.

The present invention provides a pharmaceutical composition that includes a pharmaceutical carrier comprising gas pockets containing carbon monoxide gas, wherein the pharmaceutical carrier is a foam, a solid, or a hydrogel. The present invention also provides methods of using the pharmaceutical composition to treat an inflammatory disease or condition, and methods of making the pharmaceutical composition.

Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the term "and/or" can include any and all combinations of one or more of the associated listed items.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Also herein, where a range of numerical values is provided, it is understood that each intervening value is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

As used herein, the terms "treatment," "treating," and the like, refer to obtaining a desired pharmacologic or physiologic effect. The effect may be therapeutic in terms of a partial or complete cure for an inflammatory disease or condition, or an adverse effect attributable to the disease or disorder. "Treatment," as used herein, covers any treatment of a disease or disorder in a mammal, particularly in a human, and can include inhibiting the disease or condition, i.e., arresting its development; and relieving the disease, i.e., causing regression of the disease.

As used herein, the term "prevention" includes either preventing the onset of a clinically evident inflammatory disease or condition altogether or preventing the onset of a preclinically evident stage of inflammation in individuals at risk. This includes prophylactic treatment of those having an enhanced risk of developing an inflammatory disease or condition.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

For methods of prevention in a human or animal subject, the subject is preferably a subject at risk of acquiring an inflammatory disease or condition, such as inflammatory bowel disease. The subject may be at risk of inflammation due to smoking, obesity, older age, stress, an unhealthy diet, being genetically predisposed to inflammation, and so on.

"Pharmaceutically acceptable" as used herein means that the compound or composition is suitable for administration to a subject to achieve the treatments described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as the inhibition of an enzyme by a detectable amount.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts at toxic concentrations, does not cause prolonged inflammation or irritation, or does not induce more than a basal immune reaction in the host.

Gas Entrapping Materials

In one aspect, the present invention provides a pharmaceutical composition that includes a pharmaceutical carrier capable of entrapping carbon monoxide gas, wherein the pharmaceutical carrier is a foam, a solid, or a hydrogel. The pharmaceutical compositions are also referred to herein as gas entrapping materials (GEMs).

Pharmaceutical compositions that encapsulate a relatively high percentage of carbon monoxide through pressurization with carbon monoxide through different methods into different pharmaceutical carriers are described. This was accomplished using both liquid and solid formulations including a multicomponent formulation contained a foaming agent(s) and thickening agent(s) to create a foam product, and a multicomponent foam-gel system that also used foaming agent(s) and thickening agents(s) dispensed into a crosslinked solution, a solidified sugar matrix to trap the gas, and other solid or liquid products that are safe and able to trap air bubbles in a liquid or solid matrix. For liquid matrices, a formulation was developed that uses thickening and foaming agents to encapsulate carbon monoxide gas within a liquid matrix to produce a colloidal foam that is a high-volume percent carbon monoxide.

Pharmaceutical compositions are materials that can be used for treatment or prevention of diseases or conditions. Preferably, pharmaceutical compositions enable the delivery of an active agent (e.g., carbon monoxide) to a subject with a suitable pharmacokinetics to facilitate the action of the active agent within the subject. Preferably, the pharmaceutical composition is also safe and biocompatible for the subject.

In some embodiments, the pharmaceutical composition provides extended release of carbon monoxide gas. Extended release, as used herein, refers to release of the carbon monoxide gas over an extended period of time, rather than releasing the gas in a relatively short burst. In some embodiments, the extended release releases the carbon monoxide at a relatively constant rate, which may be predetermined. Extended release can be the result of the gradual breakdown of the pharmaceutical carrier in an in vivo environment. In some embodiments, the pharmaceutical composition provides release of carbon monoxide gas for up to 24 hours. In other embodiments, the pharmaceutical composition provides a release of carbon monoxide gas for up to 18 hours, up to 12 hours, or up to 6 hours. In further embodiments, the release is for from 4 to 24 hours, from 2 to 12 hours, or from 1 to 8 hours.

The pharmaceutical compositions include a pharmaceutical carrier. The pharmaceutical carrier is the material that carries the active agent (e.g., carbon monoxide gas). The carrier may take a wide variety of forms depending on the form of preparation desired for administration, e.g., oral or rectal. For example, the carrier may have a capsular, cylindrical, or spherical form. Examples of suitable pharmaceutical carriers include foams, solids, and hydrogels.

The pharmaceutical carrier is capable of entrapping carbon monoxide gas, and typically comprises gas pockets containing carbon monoxide gas. The pockets are holes or bubbles within the material of the pharmaceutical carrier, and serve the function of entrapping carbon monoxide within the pharmaceutical carrier. Accordingly, the pharmaceutical compositions can also be referred to as "gas entrapping materials." The size of the holes or bubbles within the material varies depending on the method of making the pharmaceutical composition, as well as the material used to form the pharmaceutical carrier. In some embodiments, the holes or bubbles have a diameter ranging from 10 μm to 500 μm, while in other embodiments the holes or bubbles have a diameter ranging from 20 μm to 400 μm, or from 30 μm to 300 μm. The median diameter of the holes or bubbles can be about 30 μm, about 40 μm, about 50 μm, about 60 μm, about 70 μm, about 80 μm, about 90 μm, or about 100 μm. In some embodiments, the holes or bubbles are isolated from one another (i.e., closed-cell), while in other embodiments the holes or bubbles are at least partially connected to form a matrix (i.e., open-cell).

The gas pockets can contain 100% carbon monoxide gas, or the gas pockets may contain a mixture of carbon monoxide gas and one or more other gases. For example, the gas pockets can contain carbon monoxide gas together with the gases present in air (primarily oxygen and nitrogen gas). In some embodiments, the gas pockets can include carbon monoxide gas together with one or more additional gases, such as nitric oxide, carbon dioxide, or hydrogen sulfide.

Preferably the pharmaceutical carrier is capable of entrapping a relatively high amount of carbon monoxide gas. The concentration of carbon monoxide gas that is entrapped within the pharmaceutical carrier varies depending on the pressure of the carbon monoxide when it is contacted with the pharmaceutical carrier, and the composition of the pharmaceutical carrier itself. The amount of carbon monoxide entrapped by the pharmaceutical carrier can vary from about 0.1 mg/g to about 1.0 mg/g (of the weight of CO compared to the weight of the carrier), or from about 0.3 mg/g to about 0.7 gm/g, or from about 0.4 mg/g to about 0.6 mg/g. In various embodiments, the concentration of carbon monoxide gas can be at least 0.1 mg/g, at least 0.2 mg/g, at least 0.3 mg/g, at least 0.4 mg/g, at least is at least 0.5 mg/g, at least 0.6 mg/g, at least 0.7 mg/g, at least 0.8 mg/g, at least 0.9 mg/g, or at least 1.0 mg/g.

In some embodiments, the pharmaceutical carrier is a foam. A foam is a substance made by trapping air or gas bubbles inside a liquid or semi-solid. Typically, the volume of gas is much larger than that of the liquid, with thin films separating gas pockets. Preferably, the foam is stable for at least a minute, and is both biodegradable and biocompatible. The foam a plurality of polymeric thickening agents selected from the group consisting of locust bean gum, a sodium alginate, a sodium caseinate, an egg albumin, a gelatin agar, a carrageenin gum, a xanthan gum, a quince seed extract, a tragacanth gum, a guar gum, a cationic guar, a hydroxypropyl guar gum, a starch, an amine-bearing polymer, a chitosan, an alginic acid, a hyaluronic acid, a chemically modified starch, a carboxyvinyl polymer, a polyvinyl alcohol, a polyacrylic acid polymer, a polymethacrylic acid polymer, a polyvinyl acetate, a polyvinyl chloride polymer, a polyvinylidene chloride polymer, a methylcellulose, a hydroxypropyl cellulose, a hydroxypropyl methylcellulose, a hydroxyethyl cellulose, a methylhydroxyethylcellulose, a hydroxyethylcarboxymethylcellulose, a carboxymethyl cellulose, a cationic cellulose, a PEG 1000, a PEG 4000, a PEG 6000, a PEG 8000, and a carbomer.

In some embodiments, the foam system includes a starchy thickener compound (e.g., maltodextrin), a polymeric cellulose-derived foaming agent (e.g., methylcellulose) and a thickener compound (e.g. xanthan gum). In a preferred embodiment, the foam system uses a combination of methylcellulose as a primary foaming agent and maltodextrin and xanthan gum as thickening agents to produce a stable, thin foam. These can be combined at different ratios to produce foams with different characteristics. For the present invention, a foam that is stable for a few minutes before becoming a liquid to allow for quick degradation and release in the body was desired. The inventors have shown a variety of foams using different concentrations and different characteristics to use in different applications.

The foam composition includes primarily water, with less than 5% by weight of foaming and thickening compounds. In some embodiments, the foaming and thickening compounds include maltodextrin, methylcellulose, and xanthan gum. The ratio of the methylcellulose to maltodextrin by weight percent can be from about 0.6:1 to about 1:1, or about 0.8:1, while the ratio of maltodextrin to xanthan gum can be from about 2.5:1 to about 1.5 to 1, or about 2:1 by weight percent. In some embodiments, the amount of methylcellulose in the foam composition can be from about 0.4% to about 1.2% by weight, about 0.6% to about 1.0% by weight, or about 0.8% by weight. In some embodiments, the amount of maltodextrin can be from about 0.5% to about 1.5% by weight, from about 0.8% to about 1.2% by weight, or about 1% by weight. In some embodiments, the amount of xanthan gum can be from about 0.2% to about 1% by weight, from about 0.4% to about 0.6% by weight, or about 0.5% by weight.

Table 1 shows a number of liquid matrices that were tested to optimize the carbon monoxide encapsulation and delivery for the liquid foam system. For qualitative review, foams were rated on a scale of 1-5, 5 being the best and 1 being the worst, and + or − in the viscosity and stability rating indicate if a solution was too viscous/stable, or not viscous/stable enough, respectively. This table includes multiple foaming and thickening agents in different ratios with three components in one system. These foams were evaluated to optimize the main criteria stated in previous sections, specifically, best (i.e., most) gas incorporation, ease of use in producing both the solution and foam, ease of administration into the rectum or orally, and effective delivery of carbon monoxide to targeted areas. The final chosen foam was optimized for a low dose rectally administered foam for quick release carbon monoxide, however this is may not be the optimized foam for a different application, such as an orally administered foam, or a slower release foam. Many of the other formulations that were developed could be better in different applications compared to the final chosen formula. If given desired characteristics and applications, this table could be used to propose a formulation and further optimize after certain tests.

TABLE 1

| | Other Foaming Agents (% w/v) | Methylcellulose Type | Methylcellulose (% w/v) | Maltodextrin (% w/v) | Xanthan Gum (% w/v) | Stability | Viscosity | ease of use and mixing | Visual CO encapsulation |
|---|---|---|---|---|---|---|---|---|---|
| | | | | | Liquid Foam Formulations | | | | |
| 1 | | 4000 cPs | 0.5-1% | 0% | 0 | 2+ | 1+ | 1 | — |
| 2 | | 1500 cPs | 0.5-1% | 0% | 0 | 2+ | 2+ | 1 | — |
| 3 | | 15 cPs | 1-2% | 0% | 0.15% | 2− | 3− | 3 | — |
| 4 | | F50 | 1% | 0% | 0.15% | 2− | 3− | 3 | — |
| 5 | | F50 | 1% | 0% | 0.30% | 2− | 3− | 5 | — |
| 6 | | F50 | 1% | 0% | 0.60% | 3− | 4− | 5 | — |
| 7 | | A4C | 1% | 0% | 0.60% | 3− | 4− | 5 | — |
| 8 | | A4C | 1% | 1% | 0.60% | 5 | 5 | 5 | — |
| 9 | | A4C | 1% | 10% | 0.60% | 3− | 2− | 3 | — |
| 10 | | A4C | 1% | 5% | 0.60% | 3− | 4− | 3 | — |
| 11 | | A4C | 1% | 5% | 0.75% | 3− | 4− | 3 | — |
| 12 | | A4C | 1% | 1% | 0.75% | 4+ | 4+ | 5 | 4 |
| 13 | | A4C | 2% | 1% | 0.75% | 3+ | 3+ | 4 | 3 |
| 14 | | A4C | 1.5% | 1% | 0.75% | 3+ | 4+ | 4 | 3 |
| 15 | | A4C | 1% | 2% | 0.75% | 4+ | 4+ | 5 | 4 |
| 16 | | A4C | 1% | 3% | 0.75% | 3+ | 4+ | 5 | 4 |
| 17 | | A4C | 1% | 1% | 0.75% | 4+ | 4+ | 5 | 4 |
| 18 | | A4C | 1.5% | 2% | 0.75% | 4+ | 3+ | 4 | 4 |
| 19 | | A4C | 1% | 2% | 0.75% | 4 | 3+ | 5 | 5 |

TABLE 1-continued

| | Liquid Foam Formulations | | | | | | | | |
|---|---|---|---|---|---|---|---|---|---|
| | Other Foaming Agents (% w/v) | Methyl-cellulose Type | Methyl-cellulose (% w/v) | Malto-dextrin (% w/v) | Xanthan Gum (% w/v) | Stability | Viscosity | ease of use and mixing | Visual CO encapsulation |
| 20 | Foam Magic-2% | | 0 | 0 | 0.40% | 5 | 5 | 4 | 4 |
| 21 | | A4C | 1% | 1% | 0.60% | 5 | 5 | 5 | 4 |
| 22 | | A4C | 0.75% | 1% | 0.75% | 4+ | 5 | 5 | 5 |
| 23 | | A4C | 0.80% | 1% | 0.50% | 5 | 5 | 5 | 5 |
| 24 | | A4C | 0.80% | 1% | 0.25% | 3− | 4− | 5 | 5 |
| 25 | | A4C | 0.80% | 1% | 0.75% | 4+ | 4+ | 5 | 5 |

In some embodiments, the pharmaceutical carrier is a hydrogel. A hydrogel is a crosslinked hydrophilic polymer that maintains a well-defined structure. In order to provide improved biocompatibility, the hydrogels used in the gas entrapping materials of the pharmaceutical composition are preferably based on natural polymers, such as hyaluronic acid, chitosan, heparin, alginate, or fibrin.

In some embodiments, the hydrogel comprises xanthan gum, methylcellulose, maltodextrin, and alginate. This hydrogel can also be considered a foam/hydrogel mix. A hydrogel gas entrapping material was developed that uses alginate as a thickening agent with a mixture of maltodextrin, methylcellulose, and xanthan gum as foaming agents and additional thickening agents.

The foam/hydrogel used as the pharmaceutical carrier can be prepared using the same materials used to prepare the foam pharmaceutical carrier, but with the addition of a crosslinking polymer (e.g., alginate). The amount of cross-linking polymer included in the foam/hydrogel composition can be from about 0.5% to about 4.0% by weight, or from about 1.0% to about 3.0% by weight, or from about 1.0% to about 2.0% by weight.

Table 2 shows various liquid formulations that were tested for the foam gel, in addition to the concentration of the cross-linking solutions that were tested and optimized. The foam-gel product is a two compound system that allows for a liquid formulation of thickening component (alginate) and foaming component (foam magic) that can be pressurized in the canister featured in FIG. 1, and then be dispensing into a cross linking formulation that will result in a stiffer hydrogel shell around the foam. The stiffness of the exterior shell is impacted by the concentration of the crosslinking solution as well as the alginate concentration, which affects the thickness of the solution as well. Finally, the foaming component, foam magic, was used to incorporate more gas into the solution when it is pressurized. Multiple design of experiments (DoE) were performed with carbon dioxide pressurized canisters to determine the correct type of alginate, concentration of alginate, concentration of foaming agent, and concentration of calcium chloride into which the foam is dispensed. The top choice candidates that were found with pressurized carbon dioxide included 1-2% modernist pantry alginate and 0.5-1% Sigma Aldrich alginate all with 2% foaming agent and they were tested with carbon monoxide at different pressures (20-100-200 PSI), which was then dispensed into different calcium chloride concentrations. Images were taken to qualitatively evaluate gas encapsulation and bubble stability. Additionally, gelatin was investigated in early trials as a thickening agent, bit not recorded because it was quickly abandoned due to it having little effect on the thickening of the foam and increasing the complexity of the system. These tests resulted in the optimum formulation for a foam-gel for the desired application, rectal administration in mice to treat IBD and prevent proctitis, which was 1.0% modernist pantry sodium alginate with 2.0% foaming agent dispensed into 100 mM calcium chloride.

TABLE 2

| Foam Gel Liquid Formulations | | | |
|---|---|---|---|
| Alginate Type | Alginate (% w/v) | Foam Magic (% w/v) | Calcium Chloride (mM) |
| Modernist Pantry | 1.0% | 2.0% | 50, 100, 200, 400 |
| Modernist Pantry | 2.0% | 2.0% | 100, 200, 400 |
| Modernist Pantry | 3.0% | 2.0% | 100, 200, 400 |
| Modernist Pantry | 0.5% | 2.0% | 50, 100, 200 |
| Modernist Pantry | 0.5% | 2.0% | 50, 100, 200, 400 |
| Modernist Pantry | 1.0% | 3.0% | 100, 200, 400 |
| Modernist Pantry | 2.0% | 3.0% | 100, 200, 400 |
| Modernist pantry | 1.0% | 6.0% | 50, 100, 200 |
| Modernist Pantry | 2.0% | 6.0% | 50, 100, 200 |
| Sigma Aldrich | 5.0% | 2.0% | 50, 100, 200, 500 |
| Sigma Aldrich | 1.0% | 2.0% | 50, 100, 200, 500 |
| Sigma Aldrich | 2.0% | 2.0% | 50, 100, 200, 500 |
| Sigma Aldrich | 0.5% | 2.0% | 50, 100, 200, 500 |
| Sigma Aldrich | 0.5% | 2.0% | 50, 100, 200 |
| Sigma Aldrich | 1.0% | 3.0% | 50, 100, 200, 500 |
| Sigma Aldrich | 1.0% | 3.0% | 50, 100, 200, 500 |
| Top Formulation | | | |
| Modernist Pantry | 1.0% | 2.0% | 100 |

In some embodiments, the pharmaceutical carrier is a solid. A solid matrix was also developed that encapsulates carbon monoxide gas. One of the advantages of providing a pharmaceutical carrier that is a solid is that solid carriers provide the most stable form of gas entrapping materials. Preferably, the solid is a biocompatible and biodegradable material such as a sugar, which can melted and used to entrap carbon monoxide gas at high pressure.

To prepare a solid pharmaceutical carrier, high pressure carbon monoxide is captured in a liquid melted sugar matrix at high temperature with mixing, and the sugar solution solidifies as it cools to capture the carbon monoxide. This product will capture a larger quantity of gas because the final product contains carbon monoxide at that high pressure as opposed to atmospheric pressure in the carbon monoxide foams. This solid sugar matrix is also significantly more stable at room temperature and atmospheric pressure and will only release the gas if it is dissolved in an aqueous solution or heated to a melting temperature. The solid pharmaceutical carrier should be stored with a desiccant because of its hygroscopic properties. This allows easy release after ingestion within the aqueous environment of the body.

A variety of different sugars are suitable for preparing the solid pharmaceutical carrier. For example, the sugar matrix can be formed from a simple or complex carbohydrate selected from glucose, fructose, sucrose, lactose, maltose, isomaltose, corn syrup and mixtures thereof. In some embodiments, the solid pharmaceutical carrier is prepared using a mixture of sucrose, lactose, and corn syrup. For example, the solid pharmaceutical carrier can include from 30% to 60% sucrose by weight, from 30% to 60% lactose by weight, and from 10% to 20% corn syrup by weight (where the combined weights add up to about 100%).

In some embodiments, the pharmaceutical composition is a stable composition. A stable composition is one that can retain its basic shape, and continue to entrap carbon monoxide, for a significant period of time. The stability of the pharmaceutical composition can vary depending on the environment in which the pharmaceutical composition is placed, and the type of pharmaceutical composition. For example, the solid pharmaceutical composition can have a higher stability when stored in a dry environment at room temperature, as compared to its stability in a warm aqueous environment (e.g., in vivo). In some embodiments, the stability of the pharmaceutical composition when stored in a dry environment at room temperature is at least one week, at least two weeks, at least 3 weeks, at least one month, at least 3 months, or at least 6 months. Foam compositions have a lower stability than the solid compositions, and are typically only stable for at least one minute, at least two minutes, at least 3 minutes, at least 10 minutes, or at least 15 minutes.

All the gas-entrapping materials can be modified using coatings to modify the characteristics of the pharmaceutical composition or create better targeted release. Examples of materials that can be used to coat the pharmaceutical compositions include polymers, biodegradable polymers, gums, cellulosics, starches, clays, colloidal (fumed silica, gel silica), fatty acids and their salts, fatty alcohols, fatty esters, butters, natural waxes (vegetable derived), synthetic waxes (petroleum derived), silicone waxes, silicone crosspolymers, or beeswax.

Treating Inflammatory Disease

Another aspect of the invention provides a method of treating an inflammatory disease or condition in a subject in need thereof. The method includes administering a therapeutically effective amount of carbon monoxide gas to the subject, wherein the carbon monoxide gas is administered using a pharmaceutical composition comprising a pharmaceutical carrier comprising gas pockets containing carbon monoxide gas, wherein the pharmaceutical carrier is a foam, a solid, or a hydrogel. The pharmaceutical composition used to administer the carbon monoxide gas can be any of the pharmaceutical compositions described herein. In some embodiments, pharmaceutical carrier is a foam, while in other embodiments the pharmaceutical carrier is a solid or a hydrogel.

The carbon monoxide entrapping pharmaceutical compositions described herein can be used to treat a variety of different inflammatory conditions and diseases. The inflammatory condition or disease can be a chronic or acute form of inflammation. A non-exclusive list of such conditions and diseases includes arthritis, allergic responses, asthma, rheumatoid arthritis, glomerulonephritis. hepatitis, transplant rejection—solid organ and hematologic, ankylosing spondylitis, antiphospholipid antibody syndrome, gout, myositis, scleroderma, psoriasis, Sjogren's syndrome, systemic lupus erythematosus, vasculitis, acute respiratory distress syndrome, multiple sclerosis, Graves' disease, Addison's disease, cytokine storm, celiac disease, ulcerative colitis, inflammatory bowel disease, myasthenia gravis, Hashimoto's thyroiditis, type 1 diabetes, and adverse events cause by immune checkpoint inhibitor therapy.

In some embodiments, the inflammatory disease or condition is a gastrointestinal inflammatory disease or condition. Examples of gastrointestinal inflammatory diseases or conditions include Crohn's disease, inflammatory bowel disease, colitis, colitis associated with immune checkpoint inhibitor therapy, celiac sprue, microscopic colitis, and pouchitis. In some embodiments, the gastrointestinal inflammatory disease is ulcerative colitis or inflammatory bowel disease.

In some embodiments, the method further comprises co-administration of an additional gas or anti-inflammatory agent. For example, in some embodiments, the method further comprises administering hydrogen sulfide or nitric oxide that has been entrapped in the gas pockets of the pharmaceutical carrier. Examples of anti-inflammatory agents that can be co-administered include non-steroidal anti-inflammatory agents such as aspirin, ibuprofen, naproxen, and indomethacin. In some embodiments, the anti-inflammatory agent is one that is typically used to treat gastrointestinal inflammatory disease. Examples of agents used to treat gastrointestinal inflammatory disease include sulfasalazine, corticosteroids, immunosuppressants such as cyclosporine, and anti-TNF antibodies such as infliximab and adalimumab. Co-administration of an additional anti-inflammatory agent includes simultaneous administration, but also includes administration at a time proximal to administration (e.g., administration before or after) of the carbon-monoxide entrapping pharmaceutical compositions described herein, so long as the administration is close enough in time for the agents to have overlapping effects.

The pharmaceutical compositions can be administered in a variety of different ways suitable for the administration of solid or semi-solid pharmaceutical forms. Examples of suitable forms of administration for the pharmaceutical compositions described herein include oral, rectal, intravaginal, and sublingual administration. In some embodiments, topical administration can also be used in order to treat inflammatory conditions present in the skin, or to provide transdermal administration of carbon monoxide. In some embodiments, the pharmaceutical composition is administered orally, while in other embodiments, the pharmaceutical composition is administered rectally.

The data obtained from the cell culture assays and animal studies can be used to determine a range of dosage for use in humans The dosage may vary depending upon the dosage form employed and the route of administration. A dose may be formulated in animal models to achieve a concentration range in the target tissue that includes the IC50 (i.e., the concentration of the test compound which achieves a half-maximal inhibition of symptoms). Such information can be used to more accurately determine useful doses in humans.

Levels of carbon monoxide in tissue may be measured, for example, by high performance liquid chromatography.

Making Gas Entrapping Materials

Another aspect of the invention provides methods of making the carbon monoxide entrapping pharmaceutical compositions described herein. In some embodiments, a method of making a foam or hydrogel pharmaceutical composition is provided, while in other embodiments a method of making a solid pharmaceutical composition is provided.

In one embodiment, a method of making a foam or hydrogel pharmaceutical composition comprising a pharmaceutical carrier comprising gas pockets containing carbon monoxide gas is provided. The method includes the steps of: a) dissolving the carrier materials (e.g., xanthan gum, methylcellulose, maltodextrin, and optionally alginate) into an aqueous solution to form a carrier solution; b) heating the carrier solution to boiling (i.e., about 100° C.); c) cooling the carrier solution to about room temperature; and d) injecting carbon monoxide gas into the carrier solution to form a foam.

In some embodiments, the pharmaceutical composition prepared by the method is a foam. The shape of the foam prepared can be determined by the shape of the container into which the foam is injected, or by the shape of the nozzle that is used to release the foam.

In some embodiments, the pharmaceutical composition is a hydrogel. Methods of preparing a hydrogel include steps a) through d) described above, but further include step e), which is cross-linking the foam to form a hydrogel. The inventors developed a foam-gel system that uses alginate as a thickening agent with a mixture of maltodextrin, methylcellulose, and xanthan gum as foaming agents and additional thickening agents. The liquid carrier material is then pressurized with carbon monoxide and dispensed into a solution of calcium chloride to crosslink the foam into a foam-gel and form a rigid wall around the exterior of the dispensed shape. This creates an exterior crosslinked hydrogel that is stiffer than the foam itself, which prevents leaking from the interior of the CO foam. When the solution exits a high pressure carbon monoxide environment and enters atmospheric pressure, the gas bubbles that have been incorporated into the liquid rapidly expand as the pressure decreases and are subsequently trapped in the liquid matrix.

In some embodiments, the carbon monoxide gas is injected using a whipping syphon. A whipping syphon is a metal container used to pressurize liquids, typically with nitrous oxide (N2O), and is typically used in food preparation. When a pressurized liquid is forced out the nozzle of the whipping syphon, the gas escapes from the liquid, aerating the liquid and turning it into a foam. The foam can range from a quickly dissolving froth to a heavy duty, dense foam.

Figures 2A, 2B, 2C, 2D:
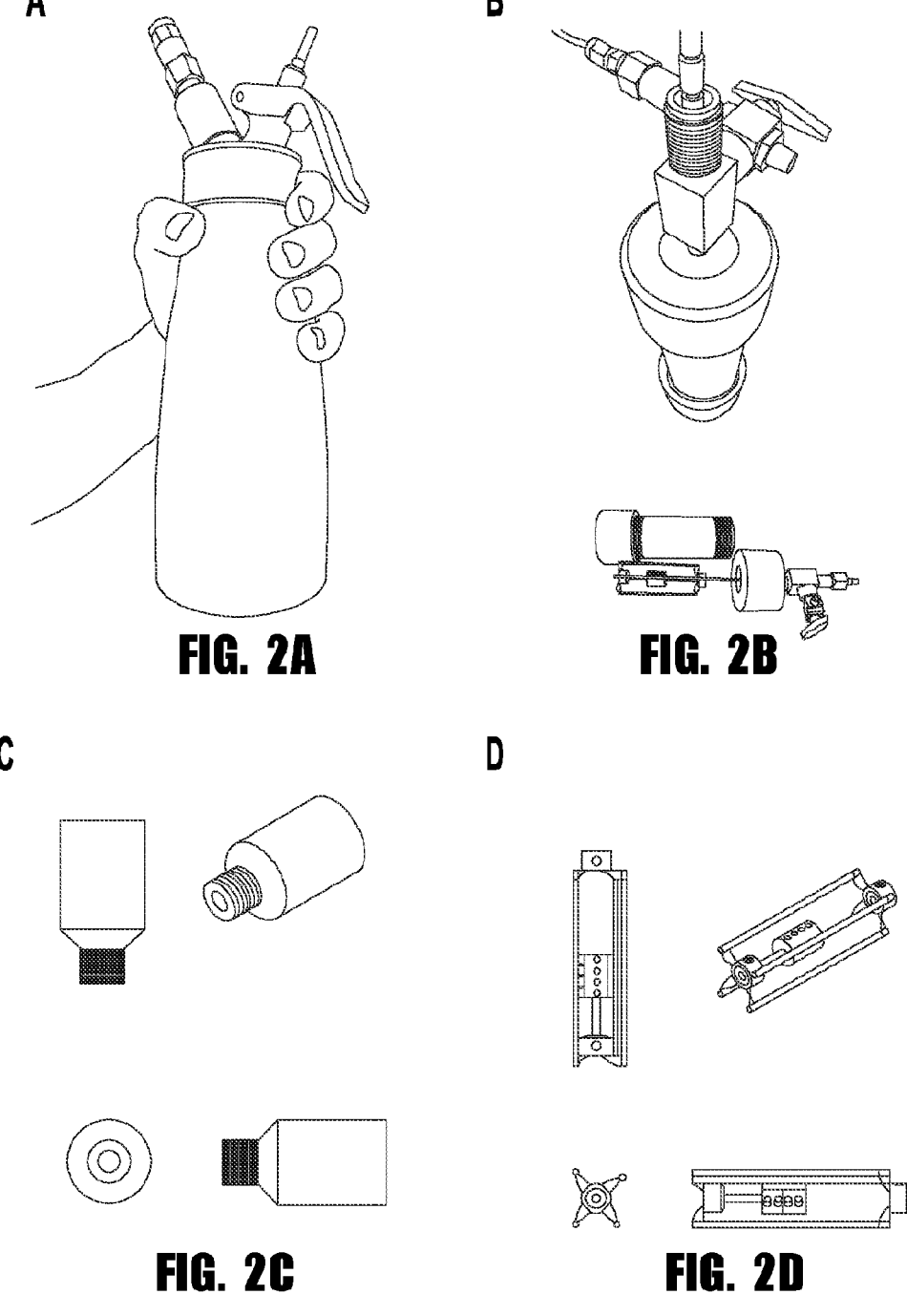
FIGS. 2A-2D provide images and schematic representations of (A) whipping siphon and (B) high-pressure reactor. Engineering drawings of (C) custom-made connector to whipping siphon and (D) stirring rod for high pressure reactor.

FIG. 2A shows the whipped cream canister with an attached modification on the inlet side of the canister that will allow the canister to be pressurized with any gas up to any pressure within the rating of the individual components. For these applications the maximum operating pressure was 200 psi, but the pressure canister system allows for up to 400 psi. A silicone cylinder from the interior of the inlet in the top piece of the canister was removed to allow for gas to freely flow into the canister, and a permanent part on the inlet side was added with a check valve to allow for one way flow of gasses from any gas tank with a proper connection. This also allowed for control over the interior pressure of the canister using a regulator. This device was used to incorporate carbon monoxide gas into liquid matrices at room temperature.

FIG. 2B shows the modified system dispensing a carbon monoxide foam that is dispensed from the pressurized canister at 200 psi to atmospheric pressure, which causes the gaseous bubbles that are incorporated into the liquid matrix to expand as the pressure of the bubbles equilibrate to atmospheric pressure. The amount of gas trapped in the liquid matrix is dependent on the characteristics of the liquid matrix and if the gas itself. This figure shows the ease of use of the pressurized system by depression of the lever on the outlet side. The rate of volume exiting the canister can easily be controlled by the distance the lever is depressed. Additionally, using this established system allows for different nozzles to easily be attached onto the outlet end of the canister. Different designs and customized nozzles could also be machined to control the diameter and shape of the dispensed foam. FIGS. 2C and 2D shown a custom-made connector for a whipping syphon and a stirring rod for stirring the high pressure reactor, which can be used together with the whipping syphon or modified system to prepare the pharmaceutical compositions described herein.

The pressure used to inject the carbon monoxide gas can be varied to increase the amount of carbon monoxide that is injected into the pharmaceutical carrier. In some embodiments, the carbon monoxide is injected at a pressure ranging from 50 to 700 psi. In other embodiments, the carbon monoxide gas is injected at a pressure ranging from 100 psi to 400 psi. In further embodiments, the carbon monoxide is injected at a pressure ranging from 200 psi to 400 psi. In yet further embodiments, the carbon monoxide is injected at a pressure ranging from 300 psi to 600 psi.

Another aspect of the invention provides a method of making a solid pharmaceutical carrier, which is the most stable product. For this product, high pressure carbon monoxide is captured in a liquid melted sugar matrix at high temperature with mixing, and the sugar solution solidifies as it cools to capture the carbon monoxide. In some embodiments, the sugar composition includes about 43 wt % sucrose, about 43 wt % lactose, and about 14 wt % corny syrup, in a water solution (not included in the weight calculation). Accordingly, the method of making a solid pharmaceutical carrier includes the steps of A) dissolving one or more sugars into an aqueous solution; b) heating the sugar solution to a temperature ranging from about 110° C. to about 140° C.; c) injecting carbon monoxide into the heated sugar solution. The carbon monoxide is typically injected under high pressure while the sugar solution is maintained at a temperature from about 110° C. to about 140° C. It is also preferable to stir the sugar solution while it is being heated. After step c), the sugar solution can be rapidly cooled to provide the solid pharmaceutical carrier including entrapped carbon monoxide.

The present invention is illustrated by the following example. It is to be understood that the particular example, materials, amounts, and procedures are to be interpreted broadly in accordance with the scope and spirit of the invention as set forth herein.

EXAMPLE

Delivery of Therapeutic Carbon Monoxide by Gas Entrapping Materials

Delivery through the GI tract is particularly promising due to the high diffusivity of CO across the epithelial barrier of the stomach and intestines. Nakao et al., J Pharmacol Exp Ther 319, 1265-1275 (2006). Moreover, the potential for local anti-inflammatory effects could enhance the application of CO for diseases affecting the GI mucosa. Here, inspired by techniques from molecular gastronomy, the development and pre-clinical evaluation of novel Gas Entrapping Materials (GEMs) for the delivery of CO through the GI tract are described. These formulations were designed using components generally regarded as safe by the FDA to support rapid clinical translation.

The formulations were tested in three small animal models associated with inflammation, including acetaminophen-induced acute liver injury, experimental colitis, and radiation-induced proctitis models. Models were selected based on reported efficacy of inhaled CO. Zheng et al., Nat Chem 10, 787-794 (2018). CO-GEMs delivered high therapeutic levels of carbon monoxide locally and systemically and reduced inflammation-associated damage in each animal model, respectively. These CO-GEMs offer entirely new modalities for the delivery of CO, enabling a spectrum of safe, effective, and potent delivery methods for enhanced translatability.

Results

Design and Fabrication of GEMs

Pressurized vessels were used to physically entrap CO in GRAS materials that can be easily administered to the GI tract through the oral cavity or rectum (FIG. 1A). Specifically, whipping siphons were adapted to generate robust foams and hydrogels (FIG. 1B, FIG. 2A). The whipping siphons were rated for pressures near 500 PSI, which provided a sufficiently large pressure range for operation. A custom-made high-pressure stirring reactor enabled creation of solid gas-filled materials (FIG. 1B, FIG. 2B), in a process similar to that used for the candy, Pop Rocks™.

These materials were evaluated by gas chromatography to quantify the amount of CO entrapped within the GEMs. It was determined that the foam, solid, and hydrogel GEMs encapsulated approximately 25 times more CO than CO-enriched Lactated Ringer's (FIG. 1C). Nakao et al., J Pharmacol Exp Ther 319, 1265-1275 (2006). A single dose of these materials resulted in higher peak COHb levels than those previously reported for GI formulations of CO (FIG. 1D, Table S1). Magierowska et al., Int J Mol Sci 17, 442 (2016); Belcher et al., PLoS One 13, e0205194 (2018); Steiger et al., J Control Release 239, 128-136 (2016). Given the peak COHb levels and ease of rectal administration of the foams, the foams were further optimized and subsequently evaluated in animal models.

CO delivery Optimization from Rectally Administered Foams

Figure 3A:
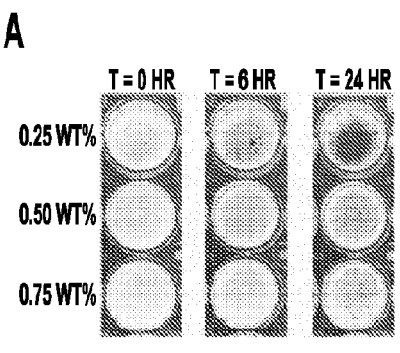
FIGS. 3A-3F provide graphs and images showing foam GEMs enabled tunable delivery of CO. (A) Foam stability at time 0, 6, and 24 hours after foam administration with different concentrations of xanthan gum. (B) Representative images of foam GEMs at different concentrations of xanthan gum at time 0, 6, and 24 hours. (C) Volumetric stability and (D) CO release kinetics from foams with different concentrations of xanthan gum over 24 hours. (E) The foam GEMs were rectally administered to mice via a rectal tube. (F) Carboxyhemoglobin as a function of canister pressure. Data are means (n=3). P values were determined by unpaired t test. NS, not significant. XG, xanthan gum. PSI, pounds per square inch.
Figure 3B:
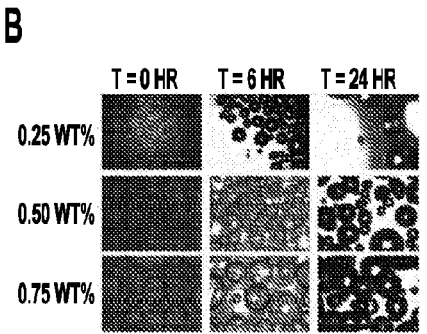
Figure 3C:
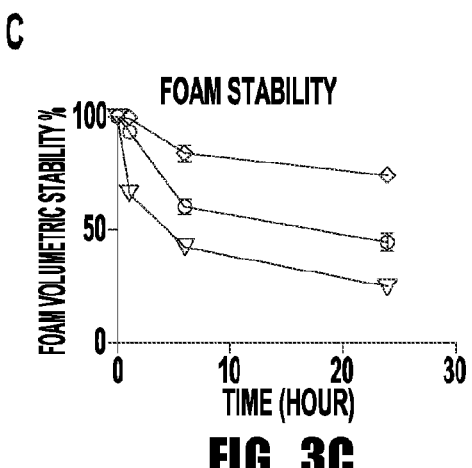
Figure 3D:
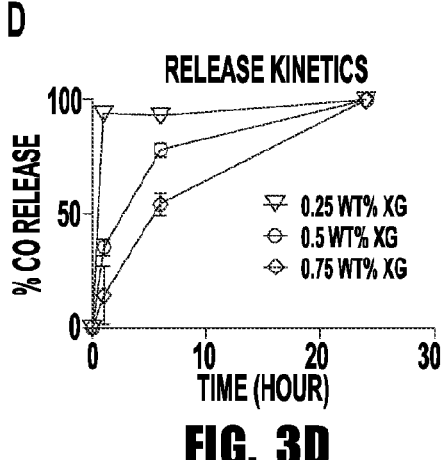
Figure 3E:
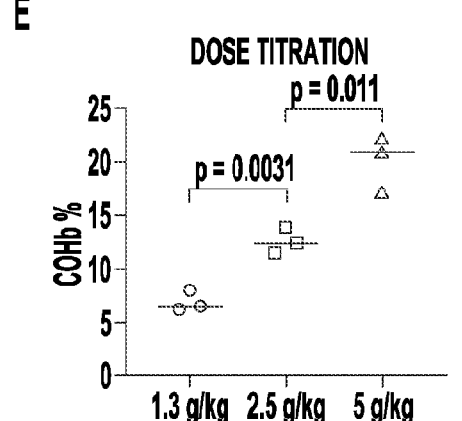
Figure 3F:
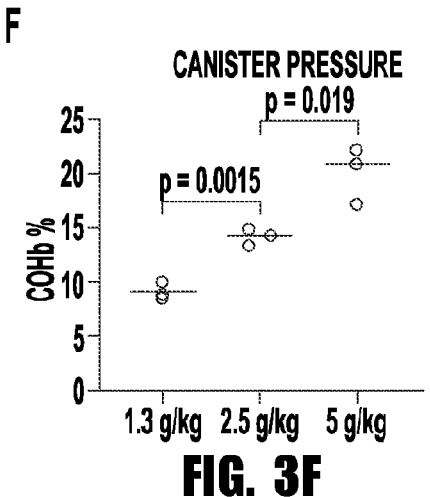
Figure 4A:
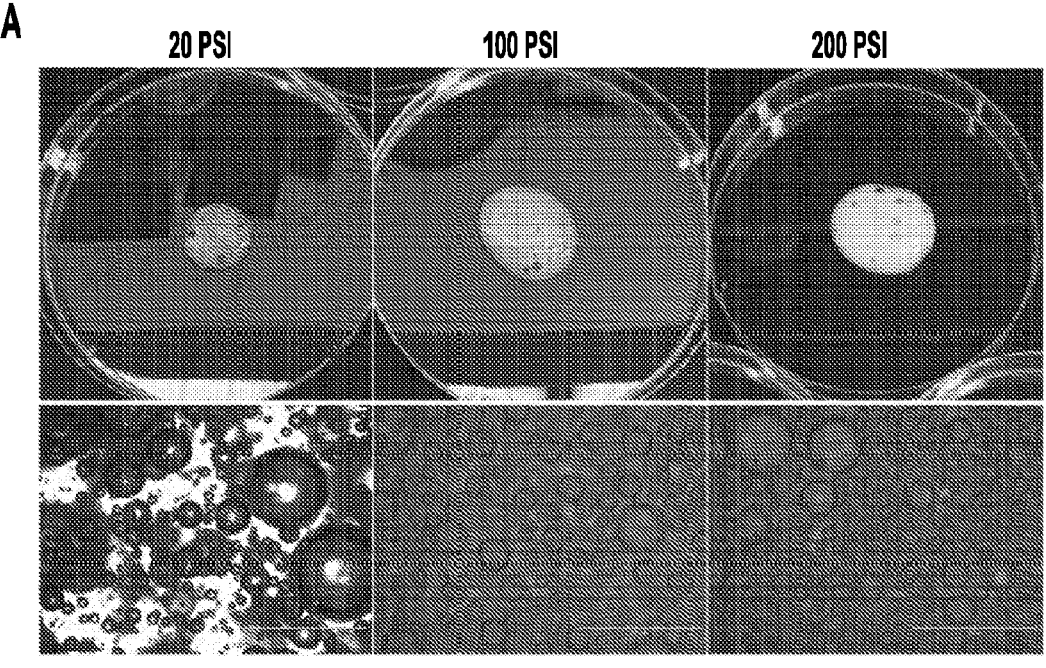
FIGS. 4A and 4B provide graphs and images showing gas entrapment as a function of pressure. (A) macroscopic and microscopic images of foams by varying pressure. (B) CO concentration as a function of canister pressure.
Figure 4B:
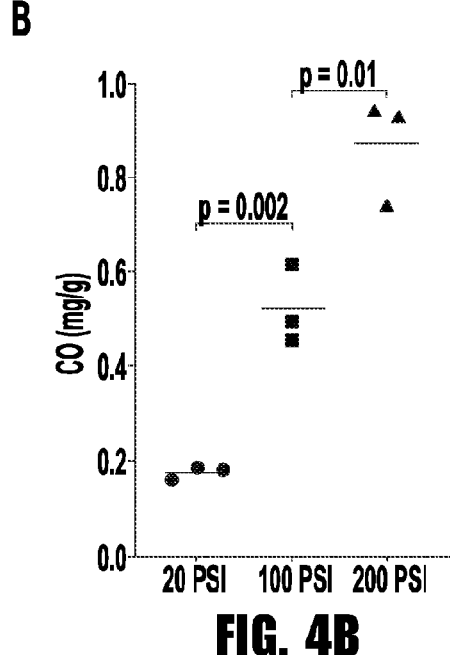

Excipient concentrations, dosing, and pressure within the whipping siphon were varied to optimize CO delivery from foams. To study these parameters, the inventors assessed visual differences in the macroscopic and microscopic appearance of the foams, volumetric foam stability and CO release kinetics, as well as maximum COHb levels in mice in vivo (FIG. 3, FIG. 4). Among the excipients within the foams, xanthan gum was found to have the greatest influence on foam stability (FIG. 3A-C). The higher the xanthan gum concentration, the more stable the foam and the slower the CO release; the 0.25 weight percentage (wt %) xanthan gum formulation was the least stable and had the fastest CO release (FIGS. 3C and D). Xanthan gum concentration had no influence on the amount of CO encapsulation. The COHb levels were found to be linearly correlated with dosing of the foams (FIG. 3E). Furthermore, pressure within the whipping siphon was found to be directly correlated with CO quantity (FIG. 4) and COHb in mice (FIG. 3F). Additional benefits of the foams are long shelf-life and the concomitant formulation with other pharmaceutical agents.

The behavior of the foams under flow conditions was also evaluated. The foams behaved like viscoelastic solids, with storage moduli (G') increasing with xanthan gum concentration and exceeding loss moduli (G") for all formulations. Additionally, all formulations were highly shear-thinning, indicative of their ease of deployment with spraying or injection. Finally, the 0.5 wt % xanthan gum foam was able to rapidly alternate between flowable and solid-like behavior at high and low shear strains, respectively and was therefore chosen for additional testing in small and large animals.

Figures 5A, 5B, 5C, 5D:
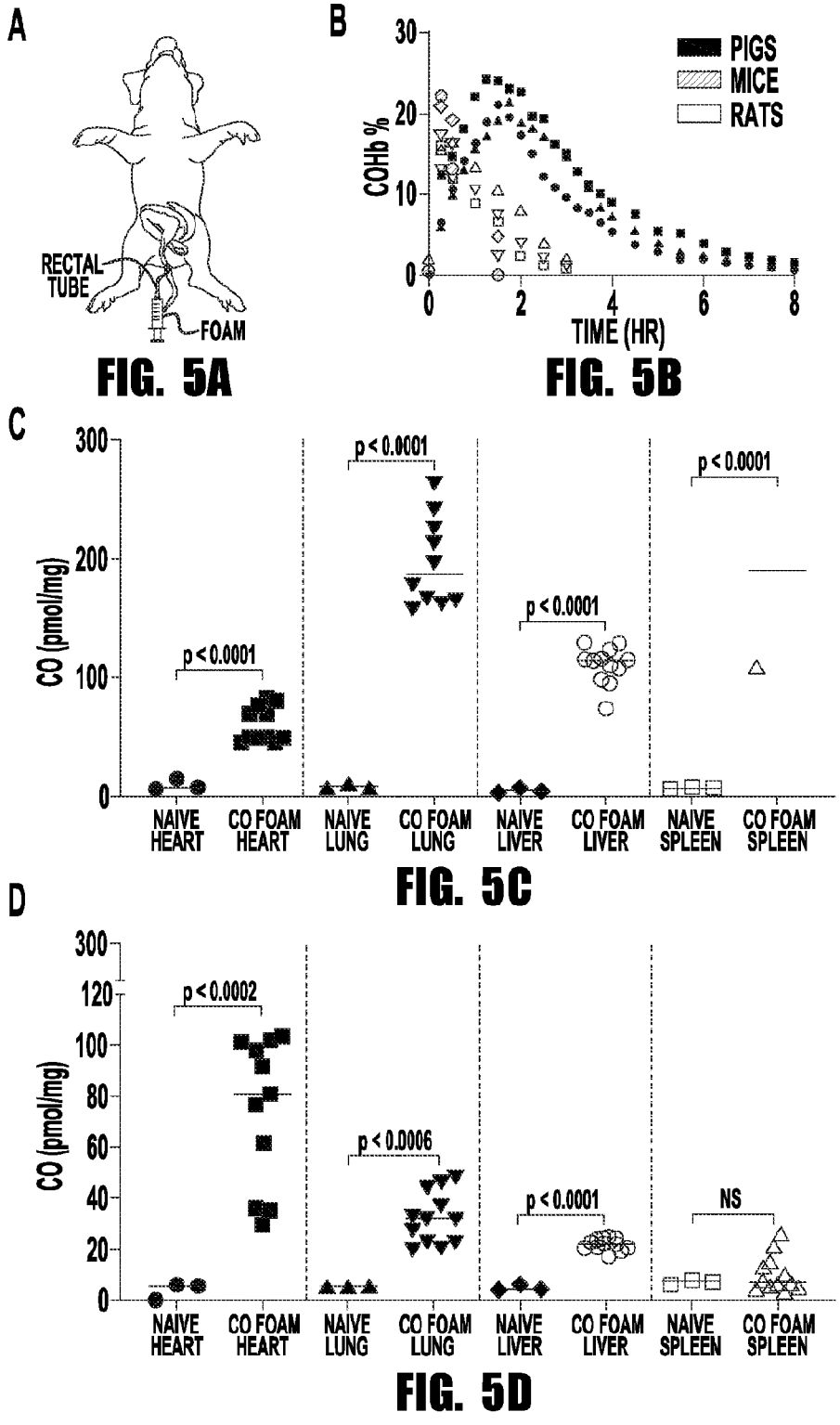
FIGS. 5A-5D provide a schematic representation and graphs showing foam GEMs achieved sustained, elevated COHb levels in both small and large animals (A) Model of foam administration to swine. (B) Carboxyhemoglobin (COHb) levels achieved in mice, rats, and swine (n=3). (C and D) Organ specific concentrations of CO at 15 minutes after foam administration intrarectally in mice (5 g/kg). Data are means (n=4). P values were determined by unpaired t test. NS, not significant. LI, large intestine. SI, small intestine. SM, skeletal muscle.

Characterization of Local and Systemic Delivery of CO in Small and Large Animals The pharmacokinetics of rectal administration of foam CO-GEMs (5 g/kg) were characterized in both small and large animals (FIGS. 5A and B). Following administration of the foams, COHb levels in mice and rats reached a maximum directly after administration and rapidly decreased over two hours that paralleled the half-life observed with inhaled CO. Watson et al., J Anal Toxicol 11, 19-23 (1987). Similarly, COHb levels increased in non-ventilated anesthetized pigs over two hours after a single dose intrarectally.

Tissue levels of CO were determined in mice that were rectally administered CO-GEMs (FIG. 5B, C). Significantly higher levels of CO were detected in numerous tissues 15 minutes after administration, especially blood-filled organs that included the liver, heart, spleen, lungs, and kidney. The small and large intestines were also found to have significantly higher CO levels compared to naïve controls.

Figures 6A, 6B, 6C:
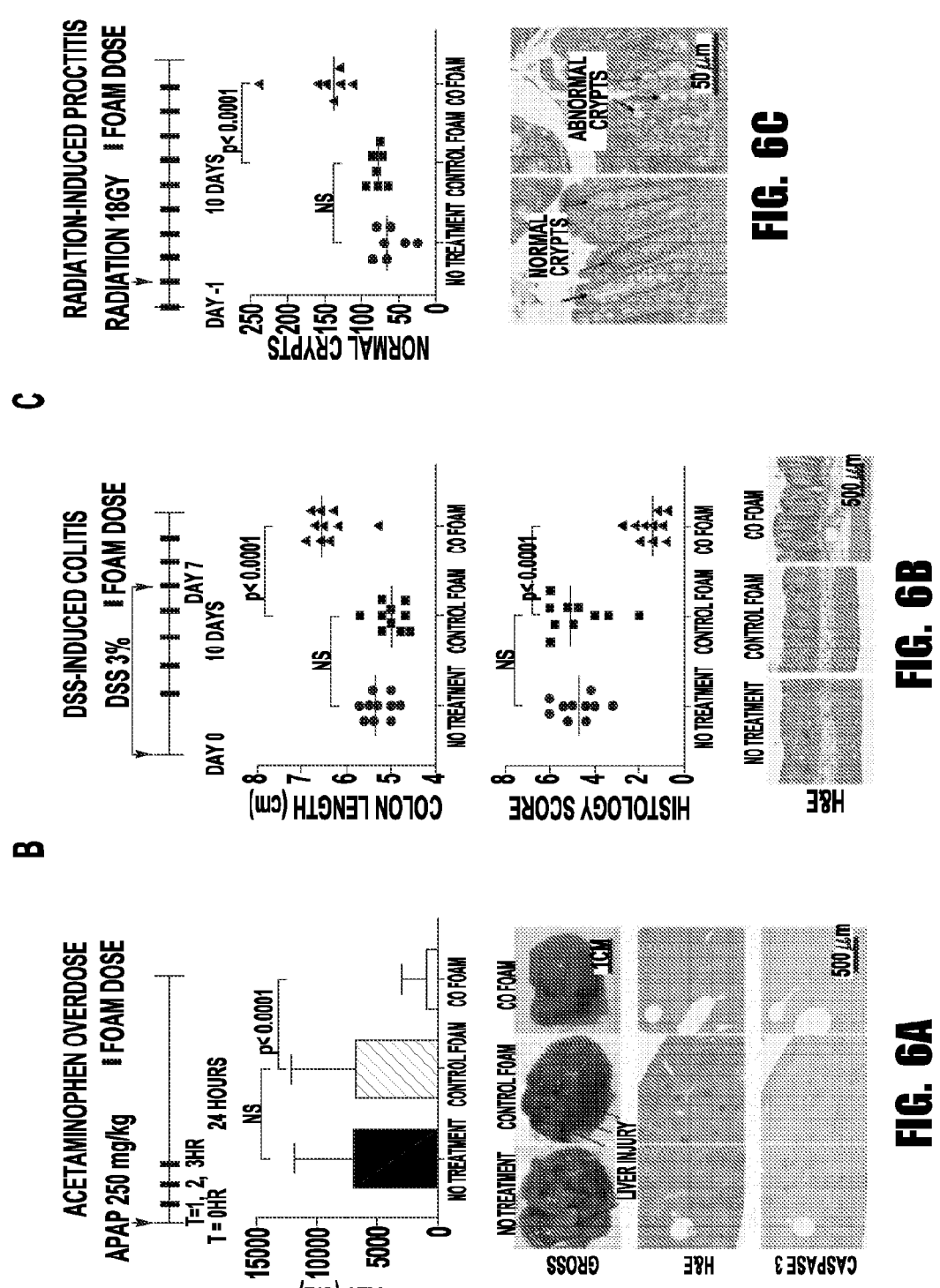
FIGS. 6A-6C provide graphs and images showing foam GEMs reduced inflammation in vivo. (A) CO foams (5 g/kg) were administered to mice at 1, 2, and 3 hours following injection of acetaminophen (250 mg/kg, IP) to cause acute liver failure. Animals that received CO foams had significantly reduced ALT levels at 24 h compared to no treatment and air foam controls (p<0.0001). Data represent means (n=15-17 per arm). P values were determined by unpaired t test. NS, not significant. Histopathology of the livers showed significant liver necrosis in controls (air foam, naïve) as measured by activated caspase 3 and H&E staining whereas livers from APAP-treated CO foam treated mice showed no activated caspase 3 and normal architecture. (B) In a model of DSS-induced experimental colitis, CO foams were administered to mice beginning on day 3 of DSS treatment and daily for 10 days thereafter. DSS-treated animals administered CO foams showed significantly longer colons (p<0.0001) and lower histology scores (p<0.0001) compared to room air foam and no treatment controls. Data represent means (n=10 per arm). P values were determined by unpaired t test. NS, not significant. (C) In a model of radiation-induced proctitis, rats were treated with CO or air foam one day prior, just before irradiation, and once daily for 8 days following exposure to 18 Gy of radiation. Animals treated with CO foams had a significantly greater number of normal intestinal crypts compared to no treatment and air foam treated control rats (p=0.0006). Data represent mean (n=7 per arm). P values were determined by unpaired t test. NS, not significant.

Rectal Delivery of CO-GEM Inhibits Acetaminophen-Induced Hepatocellular Injury To characterize the efficacy of foam GEMs on dampening inflammatory responses in a disease model, the foams were tested in a well-characterized acetaminophen (APAP) overdose model. Yan et al., Redox Biol 17, 274-283 (2018). In this model, fasted mice administered APAP intraperitoneally showed an expected radical-mediated hepatocyte cell death and a rapid pro-inflammatory response resulting in acute liver failure. In this model, mice were dosed (5 g/kg) one hour after APAP and then hourly for a total of 3 doses (FIG. 6A). These animals were compared to control mice that received room air GEM or no treatment.

Animals that received CO foam were found to have a significant reduction in hepatocellular injury compared to those that received air foam and no treatment as controls (FIG. 6A). Serum alanine aminotransferase (ALT) levels were significantly lower in animals treated with CO foams, which correlated with less caspase 3 staining and H&E staining showing reduced apoptosis, liver necrosis, and congestion, compared to controls. Livers from CO-GEM-treated mice appeared normal histologically compared to controls. Collectively, these data demonstrate the protective effects of a CO-GEM in preventing APAP-induced centrilobular congestion, hepatocellular degeneration, and coagulative necrosis.

Rectally Administered CO-GEM Protects Against Experimental Colitis

GEMs were next evaluated in the well-described experimental model of DSS-induced colitis in mice. In this model, mice were exposed to DSS for three days to induce colitis prior to initiation of CO foam treatment. Animals were maintained on DSS-containing water and foams (air or CO)

were administered once a day for an additional four days. DSS water was then stopped and daily administration of CO foam, room air foams, or no treatment were continued for an additional three days (FIG. 6B).

CO foam-treated mice showed reduced inflammation and tissue injury as evidenced by inhibition in DSS-induced colonic length shortening and reduced histology scores compared to controls and less weight loss. (FIG. 6B). Furthermore, there was reduced crypt injury, edema, and infiltration of polymorphonuclear neutrophils seen by histological staining (FIG. 6B). These data support the therapeutic benefits of CO in preventing tissue damage in the colon.

CO Foam Reduces Crypt Injury in Radiation-Induced Proctitis Model

The efficacy of CO foams in dampening inflammation and tissue damage was additionally assessed in a radiation-induced proctitis model. Rats were administered a single 18 Gy dose of radiation previously shown to induce acute proctitis within 2 weeks. Sezer et al., J Cancer Res Ther 7, 152-156 (2011) Doses of this magnitude are routinely used for cancer therapy within the pelvis for definitive or palliative intent.

Compared to air foam and no treatment controls, CO foam administered rectally pre- and post-radiation resulted in a significant reduction in intestinal crypt injury (FIG. 6C). Moreover, there was a 2-fold increase in the number of normal crypts in mice treated with CO foam compared to both air foam and no treatment controls. Weight gain was similar among all groups.

Discussion

The highly permeable nature of the GI tract allows for rapid absorption of gases, thereby positioning it as an attractive delivery pathway for the therapeutic use of CO. However, the translation of therapeutic gases from basic research into everyday treatments has remained a challenge due to numerous safety and dosing constraints. Hopper et al., Curr Pharm Des 24, 2264-2282 (2018). To address this problem, CO gas was entrapped in GRAS materials for delivery across the GI epithelium. Due to their ease of use, the GEM systems may be adapted to a variety of gasotransmitters, such as oxygen, nitric oxide and hydrogen sulfide, for various disease-related applications.

Here, the inventors show that administration of CO through foam, solid, and hydrogel GEMs can deliver titratable amounts of CO locally and systemically. They demonstrate that formulations enabling the administration of CO through non-inhaled routes are tunable and not limited by delivery materials, toxicity or potency. The preclinical results suggest that delivery of CO through these materials, in particular via rectal administration, may potentiate the anti-inflammatory effects of CO. In addition, the systems are amenable to co-administration with other therapies to improve treatment efficacy, such as in concert with powdered drug formulations.

Carbon monoxide has well-established cytoprotective effects first identified through studies of HO-1, which is implicated in numerous adaptive cellular responses to stressful stimuli and injury. Administration of CO can mimic the benefits of inducing HO-1 activity and thus endogenous CO generation during heme catalysis. This enzymatic function of HO-1 naturally produces CO that regulates a variety of intra- and extracellular cytoprotective and homeostatic effects. Tenhunen et al., Proc Natl Acad Sci USA 61, 748-755 (1968). While CO has been shown to be beneficial for numerous disease states, it may be particularly well-suited for use in regulating GI inflammation as the dense capillary network of the intestinal mucosa allows for rapid uptake of CO. Coburn, Ann NY Acad Sci 150, 13-21 (1968). Additionally, HO-1 activation has been shown to play a key role in modulating intestinal inflammation and innate immunity, and activation of this pathway through delivery of CO has already demonstrated benefit in the treatment of intestinal disease in animal models of colitis. Steiger et al., J Control Release 239, 128-136 (2016). Based on the demonstrated ability to locally deliver CO, the GEMs described herein will expand treatment options for other inflammatory pathologies of the GI tract such as inflammatory bowel diseases, radiation-induced injury, and gastroparesis. Moreover, GI administration per os or per rectum can provide simpler and potentially more effective modalities of administering CO for the management of non-GI disorders given the high diffusivity of CO. Indeed, ingestion of CORM or CO-saturated solutions have been shown to effectively treat sickle cell anemia and ischemia reperfusion of the kidney. Belcher et al., PLoS One 13, e0205194 (2018); Correa-Costa et al., Proc Natl Acad Sci USA 115, E2302-E2310 (2018). The challenge with these treatment strategies is potency, patient compliance, and safety.

While improvement was achieved in multiple small animal models of inflammation-mediated disease with these GEMs, the efficacy of these materials may be further improved by manipulating the materials to increase CO content or expand the utility of this approach with other gases such as nitric oxide or hydrogen sulfide. The pressure in the whipping siphons used to create foam and hydrogel GEMs was less than half of the pressure rating. Thus, increasing the pressure may further enhance entrapment of CO, thereby maximizing loading efficiency and reducing the volume of material needed to be delivered to achieve a therapeutic benefit. Alternative materials beyond those tested herein may enhance the volume fraction of the gas, which would also reduce the total dosing volume. Although rectal delivery of the foams was evaluated, oral delivery of the foam, solid, and hydrogel GEMs may increase the translatability of the materials given the ease and comfort of administration. Moreover, the materials enable the tunable release of CO that will broaden the number of disease indications where GEMs may be effective.

Further research will be required to better understand the safety and tolerability of GI delivery of CO. While the FDA placed a maximum safe COHb of 14% for inhalational CO, it is possible that GI delivery may enable a different therapeutic index for CO delivery based on differing pharmacodynamics and pharmacokinetics. Ji et al., J Pharm Sci 105, 406-416 (2016). There are reports that route of administration leads to drastic differences in toxicology. Insufflation of the abdomen of dogs with CO to achieve COHb levels comparable to CO administered by inhalation showed no toxicity as otherwise seen in dogs that inhaled CO. Gutierrez et al., J Appl Physiol (1985) 58, 558-563 (1985). This strongly supports investigating alternative modes of CO administration. Finally, person-to-person variability of COHb achieved between delivery modalities will be important to understand to ensure patient safety and to maximize therapeutic benefit. Hopper et al., Curr Pharm Des 24, 2264-2282 (2018).

Given the broad benefits of CO, the GEMs described may be adopted for many different clinical applications, particularly inflammation-mediated GI conditions, but also pathologies as diverse as cancer, ileus, trauma, and organ transplant among others. Ji et al., J Pharm Sci 105, 406-416

(2016) Furthermore, these materials could be extended to the concomitant delivery of other pharmacologic agents for their synergistic benefit, such as analgesics or antibiotics. In summary, this innovative approach, using safe materials, will offer entirely new modalities for the administration of therapeutic gases and treatment of inflammatory disorders.

Materials and Methods

Formulation Development

To generate the foam GEMs, a pre-foam solution was created by dissolving 0.5 wt % xanthan gum (Modernist Pantry), 0.8 wt % methylcellulose (Modernist Pantry), and 1.0 wt % maltodextrin (Sigma) in 1× phosphate buffered saline (PBS) and heating to 100° Celsius while stirring at 700 rotations per minute. The solution was cooled to room temperature and placed under vacuum to degas for 12 hours. The solution was then placed into a modified iSi 1 Pint 100 stainless steel whipping siphon with a custom-made aluminum connector to enable pressurization with any gas cylinder, including carbon monoxide and room air. The aluminum connector was fabricated using a lathe to cut the part to size and threads created using an M22 tap and ¼ NPT die (FIG. 2). The whipping siphon was purged with carbon monoxide prior to pressurizing up to 200 PSI with 99.3% carbon monoxide (Airgas). The whipping siphon was then shaken for 30 seconds prior to use and actuated into a syringe.

The hydrogel GEMs were generated using a pre-foam solution consisting of 1.0 wt % alginate (Sigma), 0.25 wt % xanthan gum, 0.8 wt % methylcellulose, and 1.0 wt % maltodextrin dissolved in 1×PBS and heated to 100 Celsius. The cooled pre-foam solution was degassed for 12 hours and then placed into the modified whipping siphon. The hydrogels were cross-linked by actuating the foam into 100 mM calcium chloride (Sigma) solution and subsequently removed.

The solid GEMs were formulated using a custom-fabricated high-pressure stirring reactor. A sugar solution was generated by dissolving 42.6 wt % sucrose, 42.6 wt % lactose, and 15.2 wt % corn syrup in water and heated to 132° Celsius while stirring. The viscous sugar solution was placed in the high-pressure reactor heated to 135 Celsius, the vessel closed, and the pressure increased to 600 PSI of 99.3% CO. The system was stirred at 750 rotations per minute for 5 minutes. Subsequently, the pressure was increased to 650 PSI and the vessel rapidly cooled using ice water and allowed to sit for 30 minutes. The solid GEMs were removed and stored with a desiccant at room temperature.

Materials Characterization

The materials were initially characterized macroscopically and microscopically. Bubbles in the foam and hydrogel GEMs were studied using an Evos microscope at 10× magnification. The solid GEMs were cut using a razor blade and visualized using a Hitachi FlexSEM 1000 II scanning electron microscope. Bubble size distribution was assessed on the foams by placement of 1 mL of foam in a 24 well plate and performing serial microscopy at designated times to assess bubble size. Furthermore, foam volumetric stability studies involved placement of 100 mL of foam into a 250 mL graduated cylinder, which were maintained in a humidified chamber at 37° Celsius. The foam volume and liquid volume fractions were recorded after visual inspection at designated times.

CO quantification in the materials was performed using an Agilent gas chromatographer-thermal conductivity detector (GC-TCD). Samples were evaluated in borosilicate glass GC vials that underwent three vacuum-nitrogen purge cycles prior to use. Foam samples were placed in vials after vacuum-nitrogen purge cycles and allowed to shake at 37° Celsius for 24 hours to release CO completely. Solid GEMs were placed in vials prior to vacuum-nitrogen purge cycles, and 1 mL of DI water was added to dissolve the solid GEMS; hydrogel GEMs were placed in vials prior to vacuum-nitrogen purge cycles and 1 mL of 0.5 M EDTA solution was added to dissolve the hydrogels. The samples were subsequently run in triplicate on the GC-TCD. Calibration curves were generated using the same 99.3% CO cylinders used to generate each GEM. Release kinetic studies were performed using dialysis tubing to mimic the lumen of the large intestine. Foam volumetric studies were performed using 250 mL graduated cylinders and evaluated visually at pre-specified times. Samples in the release kinetic and foam volumetric studies were maintained at 37° Celsius in a humidified chamber.

Rheology measurements were performed on a TA Instruments DHR-3 Rheometer using 40 mm parallel plates. All measurements were conducted at 37° C. with data averaged over 3 samples. Frequency sweeps were conducted at 1% strain, and amplitude sweeps at 10 rad/s.

Animal Studies

All procedures were approved by the Committee on Animal Care at Massachusetts Institute of Technology (MIT) (Protocol #0519-023-22, Radiation protection) and by the Institution Animal Care and Use Committee at Beth Israel Deaconess Medical Center (BIDMC) (Protocol #106-2015, Acetaminophen) and (Protocol 068-2015, DSS colitis) before initiation and all procedures described herein conform to the Committee's regulatory standards. The mice used in this study were 7-8 week old male CD-1 or C57/Bl6 mice and rats were 8-week old female Sprague-Dawley rats. Experiments were conducted at MIT Koch Institute animal facilities and BIDMC after at least 72 hours (rodents) and 7 days (swine) of acclimation. The swine used in this study were healthy female Yorkshire pigs between 65-80 kg. Animals were exposed to a 12-hour light/dark cycle and received food and water ad libitum through the studies, except when designated for experiments.

Evaluation of Pharmacokinetics of CO

Isoflurane-anesthetized mice and rats were rectally administered foams through a 5 mL syringe attached to polyethylene tubing (0.048" O.D.), with tubing inserted ~1.5 cm. In addition, isoflurane-anesthetized swine were rectally administered foams through an inflated pediatric rectal tube inserted 5 cm. In mice, blood was obtained from a lethal cardiac puncture under anesthesia; in rats, blood was obtained via tail vein, and in swine, blood was obtained from a central line accessing a jugular vein. All blood was placed into 1 mL BD syringes filled with 100 units of heparin and run on ABL80 FLEX CO-OX blood gas analyzer. For assessment of solid and hydrogel GEMs, isoflurane-anesthetized mice underwent a laparotomy with gastric incision for direct placement of pre-weighed materials (5 g/kg) into the stomach Animals underwent a cardiac puncture at 15 minutes after direct placement of foam, and blood was collected in 1 mL syringes filled with 100 units of heparin and run on the ABL80 FLEX CO-OX blood gas analyzer.

Methods for CO extraction and quantification from tissues followed previously established methods. Vreman et al., Anal Biochem 341, 280-289 (2005). The quantity of CO extracted from blood and tissue samples was measured using a reducing compound photometer GC system (GC RCP, Peak Performer 1, Peak Laboratories LLC, Mountain View, CA). A certified calibration gas (1.02 ppm CO balanced with nitrogen) was purchased from Airgas and used to generate a daily standard curve prior to experiments. Amber borosilicate glass chromatography vials (2 mL) with gas-tight silicone septa were used for all experiments and were purged of CO using a custom catalytic converter prior to the addition of calibration gas or samples. The vial headspace was flushed with CO-free carrier gas into the gas chromatography system via a custom-made double needle assembly attached to the front of the instrument.

Frozen aliquots of heparinized whole blood stored in sealed cryovials were thawed and 1 μL was injected into a purged amber chromatography vial along with 20 μL $K_3Fe(CN)_6$ using gas-tight syringes attached to repeating dispensers (Hamilton, Reno, NV). The contents in the vial were mixed thoroughly and stored on ice for a minimum of 15 minutes before CO analysis. Blood CO quantitation was reported as VolCO, the amount of CO (mL) bound to 100 mL of whole blood. Hb concentration (g/dL) was determined with the cyanmethemoglobin method using Drabkin's Reagent (RICCA Chemical Company, Arlington, TX). A standard curve was generated using a commercially available hemoglobin standard (Pointe Specific H7506STD, Canton, MI). The VolCO and Hb concentration values were used to calculate the COHb using the following equation: COHb (% sat) [(Vol)]CO×100%/([Hb]×1.34). Frozen aliquots of tissue sample were rinsed gently of external blood with chilled $KH_2PO_4$ buffer (pH 7.4) and placed into 50 mL conical tubes. Tissues were diluted to 10% (w/w) with water. With the tube submerged in ice, the tissue was diced with surgical scissors then homogenized using the Ultra-Turrax T8 grinder (IKA Works, Inc., Wilmington, NC) for 6 to 8 one-sec pulses followed by 8 to 10 one-sec pulses from an ultrasonic cell disruptor (Branson, Danbury, CT). Once completely homogenized, 10 μL of tissue homogenate and 20 μL of 20% sulfosalicylic acid were injected into the purged 2 mL amber vials with a gas-tight syringe connected to a repeating dispenser. Once injected, vials were treated as described above. CO values were reported as CO (pmol)/mg wet weight tissue.

Efficacy Studies

Acetaminophen overdose mouse model. Male CD-1 mice (Charles River) were fasted for 18 hours to deplete hepatocytic glutathione levels and then subsequently intraperitoneally (IP) injected with acetaminophen (Sigma) at 250 mg/kg. Zheng et al., Nat Chem 10, 787-794 (2018). The mice were randomized into the different conditions, including experimental (CO foam rectally administered at 5 g/kg) and controls (room air control foam rectally administered at 5 g/kg and no treatment). One hour after the IP dose of APAP, mice were treated under isoflurane every hour for three hours with CO foam, a room air control foam, or no treatment. The mice were euthanized 24 hours after the IP injection, and serum and livers collected for evaluation. ALT analysis was performed using a Catalyst DX from Idexx. The tissues were subsequently formalin fixed, processed, hematoxylin and eosin (H&E) stained, and immunohistochemically stained for caspase 3.

DSS colitis. Male C57BL/6 mice (Taconic) were randomized into the different conditions, including experimental (CO-GEM rectally administered at 5 g/kg) and controls (room air control foam rectally administered at 5 g/kg and no treatment). The mice administered 3 wt % DSS water continuously on day 1 until day 7. Starting on day 3, the mice were rectally administered CO foam, room air control foam, or no treatment under isoflurane. The mice were weighed daily prior to treatment and assessed for signs of morbidity. If there was more than 20% weight loss, the mice were euthanized, and the large intestines were collected and measured. The tissues were subsequently formalin fixed, processed, and H&E stained.

Radiation-induced proctitis. Sprague-Dawley rats (Charles River) were randomized into CO foam, room air control foam, and no treatment (n=7 per arm). Investigators and animal technicians were not blinded to arms of the study. The pathologist was blinded before and during histological analysis. No animals were excluded from analysis. One day prior to irradiation, the rats were anesthetized using 1-3% isoflurane and administered 5 g/kg rectal foams. Within 1 hour prior to irradiation, the rats were rectally administered a 5 g/kg dose of foam. For irradiation, rats were anesthetized using 1-3% isoflurane with room air and monitored using pulse oximetry. Rats were exposed to 18 Gy directed to the rectum from a single X-ray radiation source from an Xrad 320. The rats were then rectally administered CO foam, air control foam, or no treatment under isoflurane on a daily basis up until euthanasia. After completion of radiation, the animals were evaluated twice daily. Any animal that exhibited signs of morbidity or weight loss was administered buprenorphine. The animals were euthanized 9 days after completion of radiation, and tissue was formalin fixed, processed, and H&E stained. Outcome measures were defined as an extent of radiation-induced rectal injury defined as crypt injury.

Statistical Analyses

Data are expressed as means±SD. Graphs were created with GraphPad Prism software. All analyses were done using SAS v9.3. ANOVA methods were used for comparisons of continuous values between groups. Unpaired t tests were used when an overall difference was detected. Unadjusted P values were reported for pairwise comparisons when an overall difference was detected. To compare the mass of CO per mass of material between different materials, Wilcoxon rank sum tests were used and exact nominal P values were reported.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

What is claimed is:

1. A pharmaceutical composition, comprising a pharmaceutical carrier comprising gas pockets containing carbon monoxide gas having a concentration of at least 0.5 mg/g, as measured by gas-chromatography thermal conductivity, wherein the pharmaceutical carrier is a foam or a hydrogel comprising xanthan gum, methylcellulose and maltodextrin, wherein the ratio of methylcellulose to maltodextrin is from 0:6:1 to 1:1 w/w and the ratio of maltodextrin to xanthan gum is from 2.5:1 to 1.5 to 1, or a solid sugar matrix comprising glucose, fructose, sucrose, lactose, maltose, isomaltose, corn syrup or mixtures thereof.

2. The pharmaceutical composition of claim 1, wherein the pharmaceutical composition provides extended release of carbon monoxide gas.

3. The composition of claim 1, wherein the pharmaceutical carrier is a foam.

4. The composition of claim 1, wherein the foam comprises from 0.4% to 0.6% xanthan gum by weight.

5. The composition of claim 1, wherein the pharmaceutical carrier is a solid sugar matrix.

6. The composition of claim 5, wherein the sugar comprises sucrose and lactose.

7. The composition of claim 1, wherein the pharmaceutical carrier is a hydrogel.

8. The composition of claim 1, wherein the pharmaceutical carrier is a foam or a hydrogel and further comprises alginate.

9. The composition of claim 1, wherein the pharmaceutical composition is a stable composition.

10. The composition of claim 1, wherein the concentration of carbon monoxide gas is at least 0.8 mg/g.

11. The pharmaceutical composition of claim 1, wherein the foam or hydrogel is crosslinked.

12. A method of treating an inflammatory disease or condition in a subject in need thereof, comprising administering a therapeutically effective amount of carbon monoxide gas to the subject, wherein the carbon monoxide gas is administered using a pharmaceutical composition according to claim 1.

13. The method of claim 12, wherein the pharmaceutical carrier is a foam.

14. The method of claim 12, wherein the pharmaceutical carrier is a solid.

15. The method of claim 12, wherein the pharmaceutical carrier is a hydrogel.

16. The method of claim 12, wherein the pharmaceutical composition is administered orally.

17. The method of claim 12, wherein the pharmaceutical composition is administered rectally.

18. The method of claim 12, wherein the inflammatory disease or condition is a gastrointestinal inflammatory disease or condition.

19. The method of claim 12, wherein the gastrointestinal inflammatory disease is ulcerative colitis or inflammatory bowel disease.

20. The method of claim 12, wherein the method further comprises co-administration of an additional anti-inflammatory agent.

21. The method of claim 12, wherein the method further comprises administering hydrogen sulfide or nitric oxide that has been entrapped in the gas pockets of the pharmaceutical carrier.

22. A method of making a foam or hydrogel pharmaceutical composition according to claim 1 comprising a pharmaceutical carrier comprising gas pockets containing carbon monoxide gas, comprising the steps of:

a) dissolving xanthan gum, methylcellulose, maltodextrin, and optionally alginate into an aqueous solution to form a carrier solution;

b) heating the carrier solution to boiling;

c) cooling the carrier solution to about room temperature;

d) injecting carbon monoxide gas into the carrier solution to form a foam; and e) optionally crosslinking with the alginate to form a hydrogel.

23. The method of claim 22, wherein the pharmaceutical composition is a foam.

24. The method of claim 22, wherein the carbon monoxide gas is injected using a whipping siphon.

25. The method of claim 22, wherein the carbon monoxide gas is injected at a pressure ranging from 100 psi to 400 psi.

* * * * *